United States Patent [19]

Cuadra et al.

[11] Patent Number: 4,627,840
[45] Date of Patent: Dec. 9, 1986

[54] FLOW MONITORING DEVICE

[75] Inventors: Emilio Cuadra; Roberto DelValle, both of Miami, Fla.

[73] Assignee: Cordis Corporation, Miami, Fla.

[21] Appl. No.: 695,303

[22] Filed: Jan. 28, 1985

[51] Int. Cl.$^4$ .............................................. A61M 5/00
[52] U.S. Cl. ................................ 604/151; 604/246; 73/204
[58] Field of Search ................ 73/204; 604/49, 50, 604/67, 151–153, 131, 246, 891

[56] References Cited

U.S. PATENT DOCUMENTS

| | | | |
|---|---|---|---|
| 3,199,348 | 8/1965 | Salera | 73/204 |
| 3,279,251 | 10/1966 | Chanaud | 73/194 |
| 3,316,902 | 5/1967 | Winchel et al. | 128/145.5 |
| 3,326,040 | 6/1967 | Walsh | 73/204 |
| 3,535,927 | 10/1970 | Mahon et al. | 73/194 |
| 3,754,201 | 8/1973 | Adams | 73/204 |
| 3,800,592 | 4/1974 | Jones, Jr. | 73/204 |
| 3,871,229 | 3/1975 | Fletcher | 73/204 |
| 3,898,637 | 8/1975 | Wolstenholme | 340/239 R |
| 3,931,736 | 1/1976 | Elmstead | 73/204 |
| 4,003,379 | 1/1977 | Ellinwood, Jr. | 604/49 |
| 4,264,961 | 4/1981 | Nishimura et al. | 73/204 |
| 4,450,719 | 5/1984 | Nishimura et al. | 73/204 |

FOREIGN PATENT DOCUMENTS

| | | | |
|---|---|---|---|
| 2753118 | 11/1977 | Fed. Rep. of Germany . | |
| 0141618 | 11/1980 | Japan | 73/204 |
| 917198 | 1/1963 | United Kingdom | 73/204 |

OTHER PUBLICATIONS

Lilley et al, "The Use of Electronic Prediction to Achieve Fast Response from a Simple Thermal Mass Flowmeter", in Journ. of Physics E, vol. 8, #1, pp. 3–5, 1/75.
Bulletin 600 published by CGS/Datametrics, a Division of CGS Scientific Corporation of Watertown, Mass., "Heat Sensor Finds Wide Applications in Fluid Flow Measurements", 1970.

Primary Examiner—Herbert Goldstein
Attorney, Agent, or Firm—Henry W. Collins; Thomas R. Vigil

[57] ABSTRACT

The flow monitoring device is used with a pump casing on an outflow tube having a passageway therethrough with a wall thereabout. A solenoid pump communicates with the passageway for providing pulsatile liquid flow therethrough. A reduced-in-thickness area along the wall of the casing or outflow tubing has an outside surface establishing a site to measure pulsatile flow along an adjacent inside surface. A thermistor is mounted on the outside surface of the wall area for sensing the temperature thereof in response to pulsatile flow therebeneath. The thermistor is electrically energized at a predetermined level. A control circuit regulates the input of electrical energy to the thermistor for predetermined time periods. The control circuit includes a sample and hold circuit and a reset switching circuit responsive to the pump activation for supplying thermistor power after pumping begins. An amplifier in the control circuit compares differences in the input power to the thermistor during a selected time interval to measure the pulsatile flow rate through the passageway.

17 Claims, 6 Drawing Figures

FLOW MONITORING DEVICE

BACKGROUND OF THE INVENTION

1. Field of the Invention

The present invention relates to a flow monitoring device of the type including a heat sensitive sensor/transducer which forms an active part of an electronic circuit. The circuit is capable of providing a measurable electrical output related to the rate at which temperature changes at the sensor/transducer take place for analyzing periodic variations of the temperature of the sensor/transducer as a result of pulsating flow stream through a passage near the sensor/transducer. That rate of change is typically a direct measurement of the velocity of the flow stream and the electronic circuit is operable to regulate the flow rate above or below a predetermined flow rate datum for a proscribed time period.

2. Description of the Prior Art

The use of thermistors as flow sensing transducers has been proposed, particularly for controlling the flow rates of liquids such as biomedical fluids. For example, U.S. Pat. No. 3,871,229 discloses a drip flow regulator using a thermistor as the transducer for sensing flow in an intravenous system. The transducer probe is positioned in an open chamber in line with the drop path for the intravenous fluid. The transducer consists of a thermistor insulated by a glass tube. That physical construction is needlessly complicated as it requires insulated wiring to and from the transducer as well as sealing for the wires at the entrance and exit from the open chamber. The temperature of impinging drops causes thermal exchange between each drop and the transducer resulting in an output which manifests a change of resistance in the circuit connected to the thermistor. Typically, such thermistor has a characteristic where the current increases linearly with voltage until self heating occurs whereby a drop in resistance permits continued current increase without further increase in voltage. It is this characteristic called the "negative volt-ampere" which is sometimes taken advantage of to provide an amplifiable signal which is compared with a standard reference datum for determining the drip rate and for maintaining the drip rate with a desired range.

U.S. Pat. No. 3,316,902 discloses a thermistor which is positioned in the nostril of an infant to monitor respiration. The flow of air directed past the thermistor provides a signal useful in measuring rate and continuity for purposes of signaling an alarm in connection with changes in or lack of respiration.

Typical of the use of thermistors for monitoring the flow of constant temperature fluid is the system disclosed in U.S. Pat. No. 3,199,348 in which a change of thermistor impedance occurs as a result of varying temperature of the flowing fluid. Another thermistor disclosed in U.S. Pat. No. 3,075,515 is used as a leg in a Wheatstone bridge circuit forming part of a blood flow measuring system.

In the system disclosed in U.S. Pat. No. 3,326,040, two thermistors are used to measure changes in the ambient temperature as well as changes in the flow in fluid temperatures whereby ambient conditions can be taken into account to improve the sensitivity of the thermistor used for measurement of flow.

In Bulletin 600 published by CGS/DATAMETRICS, a division of CGS Scientific Corporation of Watertown, Mass. entitled "Heat Sensor Finds Wide Applications in Fluid Flow Measurements" there is disclosed a heated sensor that is part of a bridge circuit that furnishes electric heating power to the sensor to maintain the temperature of the sensor above the ambient temperature upstream of the liquid flow.

Similarly, a flow meter operating on a temperature difference between sensors that are situated in legs of a bridge circuit is disclosed in German printed patent application number 27 53 118.

Other systems for monitoring a flowing liquid are disclosed in U.S. Pat. Nos. 3,279,251; 3,535,927; and 3,898,637.

While the foregoing patents and publications disclose a variety of uses of thermistors to measure fluid flows of gases or liquids none are specifically adapted to monitoring pulsatile flow nor is there any appreciation of the importance of controlling the transducer to react at a specific time relative to the periodicity of the flowing fluid. These requirements are critical to the measurement of flow of fluid in a drug delivery system.

SUMMARY OF THE INVENTION

According to the invention there is provided a pulsatile flow monitoring device for use in an implantable drug delivery system which includes a solenoid actuated pump and which delivers a drug in quantatized liquid doses at measured intervals. The pulsatile flow monitoring device comprises a liquid conduit for conveying liquid drug doses. The conduit has a wall establishing a lumen in the conduit and an inside wall surface and an outside wall surface. The conduit wall also has a portion of normal thickness and a reduced-in-thickness portion which is at least moderately thermally conductive. A temperature sensor is mounted to the liquid conduit on the outside surface of the reduced-in-thickness wall portion for transducing the temperature of the reduced-in-thickness wall portion. The temperature varies with the flow of liquid drug doses. An electrical power supply is coupled to the temperature sensor for providing electrical energy to the temperature sensor. A regulating circuit is coupling to the power supply for determining a rate at which electrical energy is provided to the temperature sensor during preselected and discrete power delivery intervals. A measuring circuit is coupled to the power supply and temperature sensor for measuring the rate parameters at which electrical energy is consumed by the temperature sensor. Consumption rate is proportional to the reduced-in-thickness wall temperature of the conduit and proportional to the flow of liquid drug doses.

Further according to the invention there is provided a method of monitoring pulsatile flow in an implantable drug delivery system which has a solenoid activated pump and which employs a monitoring device including a liquid conduit having a reduced-in-thickness wall, a temperature sensor for sensing the reduced-in-thickness wall temperature, an electrical power supply for providing energy to the temperature sensor, a regulating circuit coupled to the power supply and the temperature sensor and a measuring circuit for measuring the rate at which electrical energy is consumed by the temperature sensor the method comprising the steps of: activating the regulating circuit to provide electrical energy to the temperature sensor for a power delivery interval which includes a preselected anticipation interval before the solenoid activates a given pump stroke in the delivery system; deactivating the regulating circuit to end the power delivery interval after a preselected maintenance interval, the preselected maintenance interval terminating after the solenoid activates a given pump stroke in the delivery system but before a successive pump stroke; and measuring the rate parameters of energy consumption by the temperature sensor with the measuring circuit during the power delivery interval.

DESCRIPTION OF THE PREFERRED EMBODIMENT

The flow monitoring device of the present invention is used in an implantable drug delivery system where it is important to measure fluid flow for proper operation of the drug delivery system. In this respect, failure to deliver a proper amount of medication to a patient can result in a lack of proper treatment producing serious complications.

There are several conditions that can cause a drug delivery system to malfunction and not provide the required amount of drug at the prescribed rate. Two of these conditions are obstructed tubing and leaky valves. Another condition influencing drug delivery occurs in the presence of air in the system which can cause an air lock, flow variations, or blockage. Consequently, in an implanted drug delivery system the operation of same may seem acceptable by the actual medication delivery may result in serious life threatening situations since the proper amount of drug may not be timely delivered. These aforesaid conditions and their related problems exist in drug delivery systems available on the market today.

Accordingly, it is desirable to provide a flow monitoring device which is able to measure the drug flow through a delivery tubing and determine if a failure has occurred. In addition, the flow monitoring device must be sufficiently sensitive in order to be capable of determining which condition is causing the failure, i.e., a leaky valve, an obstruction, air in the system or other problem.

Figure 1:
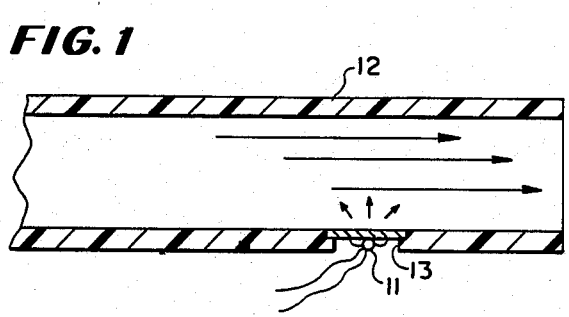
FIG. 1 is an axial sectional view of an outflow tube and shows the adhesive mounting of a flow monitoring sensor to a reduced-in-thickness wall area of the wall of the tube.

In one preferred embodiment of the flow monitoring device of the present invention shown in FIG. 1, a thermistor 11 is mounted on a hollow polymeric outflow tubing 12 and the flow of fluid therein, as shown by arrows, is measured through a reduced-in-thickness titanium wall area 13 mounted in an opening 14 in the tubing 12.

Preferably, the thermistor 11 is a glass bead thermistor 11 which is mounted on the outside of the reduced-in-thickness wall area 13 mounted in the delivery tubing 12 by a conductive epoxy such as that sold under grade and name designation EPO-TEK H70E by Epoxy Technology, Inc. of Watertown, Mass.

Where the outflow tubing 12 is internal with respect to the patient, it may be desirable to have two tubings to provide two lumens, one lumen being provided for drug infusion and the other lumen being provided for carrying wire conductors to the thermistor 11. In addition, feedthroughs may be provided to hermetically seal the place where the wire conductors extend through a pump casing to the outflow tubing 12.

Figure 2:
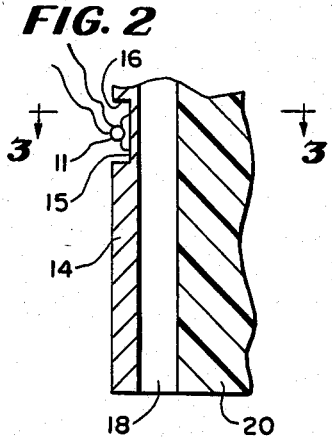
FIG. 2 is a vertical sectional view of part of a pump casing and shows the mounting of a flow monitoring sensor to a reduced-in-thickness wall area in a side wall of the pump casing wall.
Figure 3:
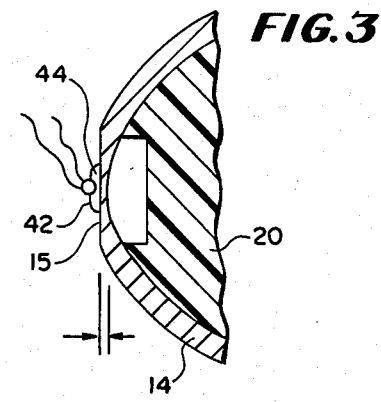
FIG. 3 is a sectional view taken along line 3—3 of FIG. 2 and shows the mounting of the flow monitoring sensor to the reduced-in-thickness wall area of the pump casing in which there is formed a drug inlet channel for liquid flow adjacent the reduced-in-thickness wall area of the pump casing wall.

Another preferred embodiment of the flow monitoring device of the present invention is shown in FIGS. 2 and 3. Here the sensor 11 is mounted on a pump casing 14 of a pump. Although not shown, and not forming part of the present invention, it will be understood that a solenoid is mounted in the pump for causing a pumping action and each pump stroke causes the thermistor 11 to change in temperature (approximately 0.02° C. resulting in a change in resistance of approximately 0.05%). The flow monitoring device is preferably used in a medication delivery system which includes a solenoid actuated pump that provides a one microliter volume of medication with each pump stroke. The flow of medication starts a few milliseconds after the solenoid pump is activated.

The thermistor 11 forms a flow sensor of the flow monitoring device and can be mounted on an outer surface 15 of a reduced-in-thickness wall area 16 of the pump casing 14 which can be mounted in a hermetically sealed pacer case or casing thereby eliminate the need for feedthroughs and the need for double lumen tubing. Mounting the thermistor 11 on the pump casing 14 within a pacer can simplify manufacturing and sealing. The flow monitoring device requires circuit design techniques to enhance the signal as a result of the mechanical thermal coupling (convective and conductive) between the fluid being measured and the sensor 11 which generally yields very small signals.

Two parameters can be used to control the power and thus heat available at the thermistor 11, namely constant temperature and constant current. The thermistor 11 may be heated, by applying current adequate to maintain the sensor a few degrees above the temperature of a pulsatile fluid flow being measured. As a result of pulses of fluid flowing through a channel 18 formed in a body member 20 within the pump casing 14, heat is transferred from the flow sensor forming thermistor 11 through the reduced-in-thickness wall area 16 to the flowing fluid and absorbed by the fluid mainly by convection, although some conduction takes place in the wall area 16 of the pump casing 14. This is possibly due to the great sensitivity of the system which results from the circuitry utilized with the thermistor 11.

It is desirable to have as large a signal output as possible from the thermistor 11 in order to have a high signal-to-noise ratio. Mechanical signal amplification is achieved by reducing the wall thickness in the reducedin-thickness area where the thermistor 11 is mounted. In particular a thickness A of 0.003 plus or minus 0.001 inch has been found to provide ease of manufacture and yield good sensitivity. The thermistor 11 is approximately 0.014 inch in diameter excluding a mound 42 of conductive epoxy mounting the thermistor 11 to the surface 15.

The thermistor 11 is mounted on the surface 15 of the reduced-in-thickness wall area 16 of the pumping casing 14 by the mound 42 of high thermally conductive epoxy adhesive in such a way as to form air pockets 44 on the sides of the mound 42 such that half of the thermistor 11 is exposed to a high thermally non-conductive medium which provides an insulative-insulating barrier to direct heat transfer. Also thermally conductive epoxy forms a large heat transfer surface area adjacent surface 15 which results in augmentation of the output signal from the thermistor sensor 11. This particular adhesive arrangement of a flow sensor forming thermistor 11 is useful to measure very minute, pulsatile flow which is typical of drug delivery systems.

The advantage of the flow monitoring device construction and circuits 22 and 37 therefore described above is the great sensitivity which allows the device to detect very minute pulsatile flow volumes with a thermistor 11 mounted outside of the fluid medium whereby damage, as a consequence of fluid contact with the sensor forming thermistor 11 and/or wire conductor therefor, are avoided. Additionally the sensor does not interfere with the fluid flow. However, utilization of the flow monitoring device is limited to conditions where the flow is pulsatile (rather than continuous) and the time at which the flow starts must be known with anticipation. The start of flow is detected with the activation of the pump solenoid.

Figure 4:
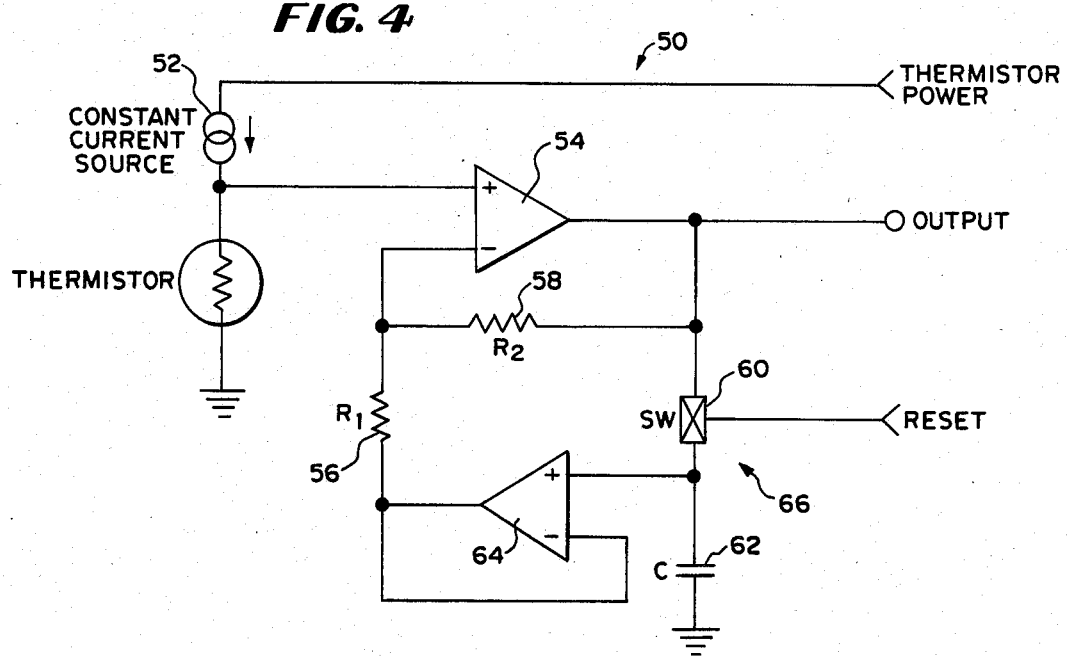
FIG. 4 is a schematic circuit diagram of an electrical circuit for selectively sampling the output signals from a flow monitoring sensor to provide a useful measurement of the rate of liquid flow. The circuit synchronizes thermistor power, amplifier reset and pump activation.

In FIG. 4 is illustrated a simplified schematic diagram of a sensor circuit 50. As shown, the thermistor 11 is powered by a constant current source 52 and the voltage developed in the thermistor 11 is amplified by a high gain operational amplifier 54, which has a gain determined by the values of resistors 56 and 58. In one preferred embodiment the gain was set to 2,200.

A switch 60 is a CMOS bilateral switch 60. The switch 60 with capacitor 62 and differential amplifier 64 form a sample and hold circuit 66 which is used for resetting amplifier 54 before each pump stroke of the solenoid pump.

Resetting the high gain amplifier 54 is necessary to provide a stable reference for the flow measurements due to the high gain of the system. If the output level were not reset, a minor change in temperature of the thermistor 11 (due perhaps to a minute change in ambient temperature) would cause a significant drift in the output of amplifier 54.

Figure 5:
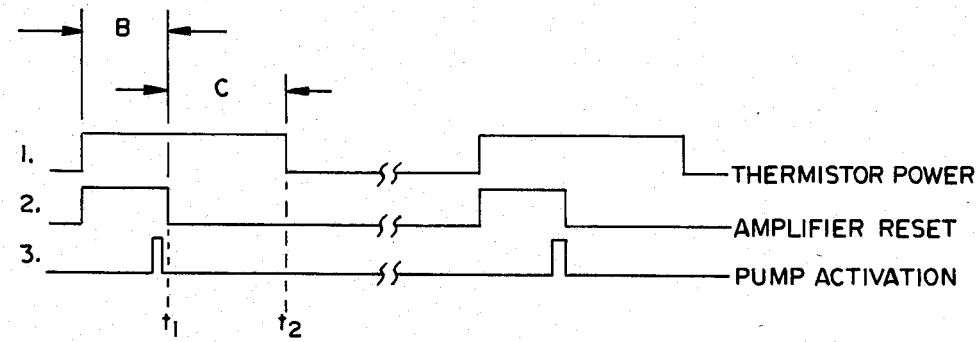
FIG. 5 is a graph of three pulse waveform diagrams necessary for operation of a transducer/sensor system constructed according to the teachings of the present invention.

FIG. 5 illustrates the signals necessary for operation of the thermistor 11. The signal labelled 1 is for thermistor power application. The second signal labelled 2 is for the amplifier reset and the third signal labelled 3 is for the solenoid or pump activation. From the time relationships of these signals 1, 2 and 3, it is apparent that the power to the thermistor 11 is applied before the pump stroke occurs, approximately a half second before. This is necessary for the thermistor 11 and adjacent parts to rise in temperature above the steady state level.

The amplifier reset signal can be applied any time between the start of the thermistor power on and a few milliseconds after the solenoid activation has ended. The precise duration of this signal is not important. The solenoid operation signal will active the pump and cause the flow the start subsequent to when this signal ends. Note the time intervals B and C in FIG. 5. Interval B is the reset time. During this time interval B, the amplifier gain is set at unity for a voltage follower function which causes output voltage to follow the thermistor voltage.

The output voltage during this time will be almost constant since the thermistor voltage, if not amplified, will change little.

Time interval C is the measurement of the interval which starts when the reset signal ends. During this interval C, any change in the thermistor voltage, in the preferred embodiment, will be amplified by a factor of 2,200 with the output starting at the reset level. When the measuring interval C ends the thermistor 11 is powered off to conserve power.

Figure 6:
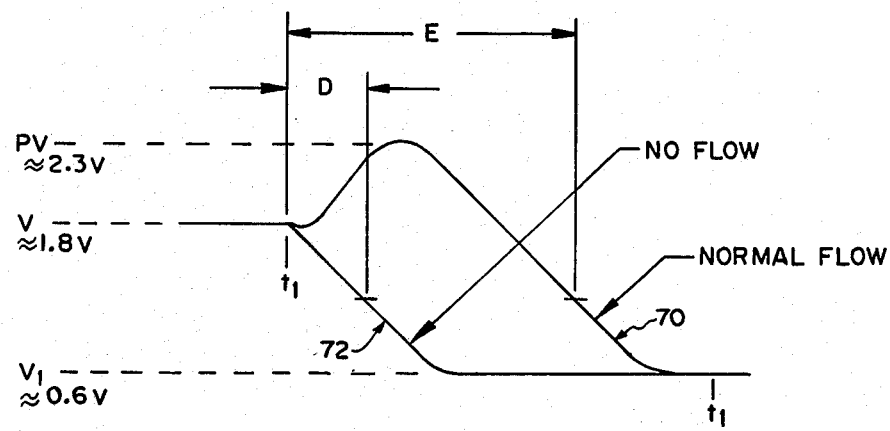
FIG. 6 is a graph of two output waveforms, one for normal flow superimposed on a waveform for a no flow condition.

In FIG. 6 are illustrated two output waveforms 70 and 72, one waveform 70 for normal flow superimposed on the waveform 72 for a no-flow situation. In the case of no-flow, the sloping (downward) line indicates that the thermistor 11 continues to increase in temperature, and its resistance drops, i.e., a negative volt-ampere condition. If there is flow, the thermistor 11 will cool off momentarily causing the peaking waveform shown.

The actual volume of flow can be quantitatively measured by either the peak voltage PV shown in FIG. 6 or by the length of time required for the signal to fall below a preset threshold level. This time interval is designated as D for the no-flow condition and E for the normal flow condition.

The flow monitoring device of the present invention is particularly designed to detect changes in the flow rate of a liquid begin output or delivered by a drug delivery system. A particular application of such a drug delivery system is in the administration of fluids to patients by means of intravenous bottles of by an implanted device which can be mounted in a pacemaker case or casing and where it is necessary to detect continuity of pulsatile flow conditions. For example, it is desirable to detect a flow rate increase or decrease with respect to time. It is also desirable to detect leakage in any valves or delivery lines of the drug delivery system. Further it is desirable to detect air bubbles or the blockage in the drug delivery line. The flow monitoring device of the present invention enables one to easily and automatically monitor such conditions.

Moreover, the flow monitoring device of the present invention has a number of advantages, some of which have been described above and others of which are inherent in the invention. In particular, the flow monitoring device of the present invention is highly sensitive to changes in pulsatile flow rate; it functions independently of ambient conditions such as the temperature of the drug being delivered; it has a wide dynamic range being capable of monitoring varying ranges of pulsatile flow rates; and lastly, it is very compatible with an implanted drug delivery system.

Also it will be apparent to those skilled in the art that modifications can be made to the flow monitoring device of the present invention without departing from the teachings of the present invention. Accordingly, the scope of the invention is only to be limited as necessitated by the accompanying claims.

We claim:

1. A pulsatile flow monitoring device in combination with an implantagle drug delivery system which includes a solenoid actuated pump and which delivers a drug in quantatized liquid doses at measured intervals, said pulsatile flow monitoring device comprising:

a liquid conduit for conveying liquid drug doses, said conduit having a wall establishing a lumen in said conduit and an inside wall surface and an outside wall surface, said conduit wall having a portion of normal thickness and a reduced-in-thickness portion which is at least moderately thermally conductive;

temperature sensing means mounted to said liquid conduit on the outside surface of the reduced-in-thickness wall portion for transducing the temperature of the reduced-in-thickness wall portion, the temperature of which varies with the flow of liquid drug doses;

an electrical power supply coupled to said temperature sensing means for providing electrical energy to said temperature sensing means;

regulating means coupled to said power supply for determining a rate at which electrical energy is provided to said temperature sensing means during preselected and discrete power delivery intervals related to said measured intervals; and measuring means coupled to said power supply and temperature sensing means for measuring the rate parameters at which electrical energy is consumed by said temperature sensing means, the consumption rate being proportional to the reduced-in-thickness wall temperature of said conduit and thus proportional to the flow of liquid drug doses.

2. The pulsatile flow monitoring device of claim 1 wherein said temperature sensing means is mounted to said outside surface with a thermally conductive epoxy adhesive.

3. The pulsatile flow monitoring device of claim 2 wherein said temperature sensing means is mounted by a mound of conductive epoxy selectively placed between said temperature sensing means and said outside surface in such a way as to form air pockets on the sides of the mount to provide an insulative-insulating barrier to facilitate direct heat transfer to said temperature sensing means.

4. The pulsatile flow monitoring device of claim 1 wherein said measuring means is activated periodically during the discrete power delivery interval in coordination with the operation of a pulsatile flow causing pump in the implantable drug delivery system.

5. The pulsatile flow monitoring device of claim 4 including a switch and reset circuit and wherein the pump includes a pump activating solenoid and said periodic activation is controlled by said switch and reset circuit responsive to operation of the solenoid.

6. The pulsatile flow monitoring device of claim 5 including a sample and hold circuit and wherein said switch and reset circuit is coupled to said sample and hold circuit for periodically monitoring said pulsatile flow.

7. The pulsatile flow monitoring device of claim 1 wherein said temperature sensing means is a thermistor.

8. The pulsatile flow monitoring device of claim 7 wherein said thermistor is initially maintained at a constant temperature by said regulating means prior to a pulse of the pulsatile flow, said regulating means is a switched constant current source, and said measuring means is responsive to the voltage variation due to resistance changes of said thermistor.

9. The pulsatile flow monitoring device of claim 8 wherein:

said regulating means includes a constant current source for supplying a constant current to said thermistor, the constant current being sufficient to maintain said thermistor at a preselected temperature above normal in the absence of fluid flow through said conduit, the constant current establishing a maintenance voltage at the thermistor when the maintained preselected temperature is reached; and said measuring means measures the time interval between the voltage at the thermistor falling from a preset voltage level to a preselected reference voltage, the preset voltage level and the preselected reference voltage being above the maintenance voltage.

10. The pulsatile flow monitoring device of claim 1 wherein said conduit is polymeric but the reduced-in-thickness portion is metallic.

11. The pulsatile flow monitoring device of claim 1 wherein said temperature sensing means is a thermistor which changes resistance in accordance with temperature of pulsatile flow adjacent said reduced-in-thickness wall area.

12. The pulsatile flow monitoring device of claim 11 wherein the reduced-in-thickness portion of the wall is metallic and is approximately 0.003 inches thick.

13. The pulsatile flow monitoring device of claim 1 wherein:

said regulating means includes a constant current source for supplying a constant current to said thermistor, the constant current being sufficient to maintain said thermistor at a preselected temperature above normal in the absence of fluid flow through said conduit; and said measuring means measures the peak voltage appearing at said thermistor.

14. A method of monitoring pulsatile flow in an implantable drug delivery system which has a solenoid activated pump and which employs a monitoring device including a liquid conduit having a reduced-in-thickness wall, temperature sensing means for sensing the reduced-in-thickness wall temperature, electrical power supply for providing energy to the temperature sensing means, regulating means coupled to the power supply and the temperature sensing means for determining a rate at which electrical energy is provided to the temperature sensing means during preselected and discrete power delivery intervals, and measuring means coupled to the power supply and the temperature sensing means for measuring the rate parameters of electrical energy consumption of the temperature sensing means, said method comprising the steps of:

activating the regulating means to provide electrical energy to the temperature sensing means for a power delivery interval which includes a preselected anticipation interval before the solenoid activates a given pump stroke in the delivery system, deactivating the regulating means to end the power delivery interval after a preselected maintenance interval, the preselected maintenance interval terminating after the solenoid activates a given pump stroke in the delivery system but before a successive pump stroke; and measuring the rate parameters of energy consumption by the temperature sensing means with the measuring means during the power delivery interval.

15. The method of monitoring pulsatile flow of claim 14 wherein:
said step of activating the regulating means is accomplished by providing a constant current to the temperature sensing means; and
said step of measuring the rate parameters of the electrical energy consumption of the temperature sensing means is accomplished by measuring the voltage at the temperature sensing means.

16. A method of monitoring pulsatile flow in an implantable drug delivery system including a solenoid activated pump, a monitoring device, a liquid conduit having a reduced-in-thickness wall, temperature sensing means for sensing the reduced-in-thickness wall temperature, an electrical power supply for providing energy to the sensing means, regulating means for determining a rate at which electrical energy is provided to the temperature sensing means during preselected and discrete power delivery intervals, and resetable measuring means for measuring the rate parameters of electrical energy consumption of the temperature sensing means relative to an electrical parameter reference, said method comprising the steps of:

activating the regulating means to provide electrical energy to the temperature sensing means for a power delivery interval which includes a preselected anticipation interval before the solenoid activates a given pump stroke in the delivery system;
deactivating the regulating means to end the power delivery interval after a preselected maintenance interval, the preselected maintenance interval terminating after the solenoid activates a given pump stroke in the delivery system but before a successive pump stroke;
reseting the resetable measuring means for providing a stable electrical parameter reference during the preselected anticipation interval; and
measuring the rate parameters of energy consumption by the temperature sensing means with the resetable measuring means during the power delivery interval after reseting the resetable measuring means.

17. The method of monitoring pulsatile flow of claim 16 wherein said step of activating the regulating means is accomplished by providing a constant current to the temperature sensing means; and said step of measuring the rate parameters of the electrical energy consumption of the temperature sensing means is accomplished by measuring voltage at the temperature sensing means.

* * * * *